(12) United States Patent
Horie (10) Patent No.: US 11,653,815 B2
(45) Date of Patent: May 23, 2023

(54) RECORDING DEVICE, IMAGE OBSERVATION DEVICE, OBSERVATION SYSTEM, CONTROL METHOD OF OBSERVATION SYSTEM, AND COMPUTER-READABLE RECORDING MEDIUM

(71) Applicant: OLYMPUS CORPORATION, Tokyo (JP)

(72) Inventor: Gen Horie, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/173,602

(22) Filed: Feb. 11, 2021

(65) Prior Publication Data
US 2021/0192836 A1 Jun. 24, 2021

Related U.S. Application Data

(63) Continuation of application No. PCT/JP2018/032248, filed on Aug. 30, 2018.

(51) Int. Cl.
*A61B 1/00* (2006.01)
*H04N 13/172* (2018.01)
(Continued)

(52) U.S. Cl.
CPC ...... *A61B 1/000095* (2022.02); *A61B 1/0002* (2013.01); *A61B 5/02108* (2013.01);
(Continued)

(58) Field of Classification Search
CPC .... G06T 15/20; H04N 13/172; H04N 13/189; A61B 1/0002; A61B 5/02108
See application file for complete search history.

(56) References Cited

U.S. PATENT DOCUMENTS 6,295,465 B1 * 9/2001 Simonetti ............... A61B 5/055
600/420
6,398,731 B1 * 6/2002 Mumm ............... G01S 7/52068
600/437
(Continued)

FOREIGN PATENT DOCUMENTS

JP 2002-282213 A 10/2002
JP 2010-279500 A 12/2010
(Continued)

OTHER PUBLICATIONS

International Search Report dated Nov. 27, 2018 issued in PCT/JP2018/032248.

*Primary Examiner* — Charles L Beard
(74) *Attorney, Agent, or Firm* — Scully, Scott, Murphy & Presser P.C.

(57) ABSTRACT

A recording device includes: a memory; and a processor including hardware. The processor is configured to generate, based on temporal change in plural sets of image data that have been generated by an endoscope and arranged chronologically, biological information on a subject, associate the plural sets of image data with the biological information to record the plural sets of image data with the biological information into the memory, and select, based on the biological information, image data from the plural sets of image data that have been recorded in the memory to generate three-dimensional image data.

4 Claims, 8 Drawing Sheets

(51) Int. Cl.
  *H04N 13/189* (2018.01)
  *A61B 5/021* (2006.01)
  *G06T 15/20* (2011.01)

(52) U.S. Cl.
  CPC ........... *G06T 15/20* (2013.01); *H04N 13/172* (2018.05); *H04N 13/189* (2018.05)

(56) References Cited

U.S. PATENT DOCUMENTS

| | | | | |
|---|---|---|---|---|
| 6,628,743 | B1* | 9/2003 | Drummond | G16H 30/20 378/15 |
| 6,674,879 | B1* | 1/2004 | Weisman | G01S 7/52088 382/128 |
| 6,889,071 | B2* | 5/2005 | Saranathan | G01R 33/567 600/413 |
| 7,522,696 | B2* | 4/2009 | Imai | G01N 23/046 378/15 |
| 8,083,679 | B1* | 12/2011 | Azuma | A61B 8/0883 600/443 |
| 8,509,511 | B2* | 8/2013 | Sakaguchi | A61B 6/12 382/131 |
| 8,577,443 | B2* | 11/2013 | Miyazaki | G01R 33/5635 600/407 |
| 8,620,044 | B2* | 12/2013 | Honda | A61B 1/00009 382/128 |
| 9,031,387 | B2* | 5/2015 | Kono | G06T 7/231 386/343 |
| 9,186,051 | B2* | 11/2015 | Hirota | G06T 7/0016 |
| 9,275,473 | B2* | 3/2016 | Hori | G06T 19/20 |
| 9,516,993 | B2* | 12/2016 | Ito | A61B 5/7246 |
| 9,521,330 | B2* | 12/2016 | Kuriyama | H04N 23/69 |
| 9,547,940 | B1* | 1/2017 | Sun | G06T 7/344 |
| 9,684,849 | B2* | 6/2017 | Yaguchi | G06T 5/50 |
| 9,959,618 | B2* | 5/2018 | Kitamura | A61B 1/041 |
| 10,010,379 | B1* | 7/2018 | Gibby | G06F 3/011 |
| 10,198,811 | B2* | 2/2019 | Kamiyama | G06T 7/0012 |
| 10,206,555 | B2* | 2/2019 | Kanda | G06V 10/60 |
| 10,210,610 | B2* | 2/2019 | Iwasaki | A61B 8/463 |
| 10,325,369 | B2* | 6/2019 | Ma | G16H 50/50 |
| 10,568,497 | B2* | 2/2020 | Nakagawa | A61B 1/05 |
| 10,679,358 | B2* | 6/2020 | On | G06T 7/248 |
| 10,732,246 | B2* | 8/2020 | Miyazaki | G01R 33/5616 |
| 10,748,279 | B2* | 8/2020 | Kitamura | G06T 7/0012 |
| 10,765,297 | B2* | 9/2020 | Kanda | G06T 7/529 |
| 10,776,921 | B2* | 9/2020 | Kitamura | G06T 7/60 |
| 10,776,998 | B1* | 9/2020 | Wang | A61B 5/1102 |
| 10,918,260 | B2* | 2/2021 | Hosoya | G16H 30/20 |
| 10,918,358 | B2* | 2/2021 | Zhang | A61B 8/0883 |
| 11,055,865 | B2* | 7/2021 | Sakamoto | G06T 7/70 |
| 11,145,053 | B2* | 10/2021 | Hayami | A61B 1/000094 |
| 11,232,568 | B2* | 1/2022 | Yamamoto | G06T 7/0014 |
| 11,232,570 | B2* | 1/2022 | Nozaki | G06T 7/0014 |
| 11,471,065 | B2* | 10/2022 | Nomura | A61B 5/316 |
| 11,565,136 | B2* | 1/2023 | Marquet | A61B 90/37 |
| 2002/0072670 | A1* | 6/2002 | Chenal | A61B 8/0883 600/449 |
| 2002/0087068 | A1* | 7/2002 | Foo | G01R 33/5673 600/413 |
| 2003/0038802 | A1* | 2/2003 | Johnson | G06T 17/30 345/420 |
| 2003/0160786 | A1* | 8/2003 | Johnson | G06T 17/20 345/419 |
| 2004/0044283 | A1* | 3/2004 | Yoneyama | G01S 7/52085 600/437 |
| 2004/0077952 | A1* | 4/2004 | Rafter | A61B 8/463 600/481 |
| 2004/0153128 | A1* | 8/2004 | Suresh | G16H 30/20 600/407 |
| 2004/0167414 | A1* | 8/2004 | Tanabe | A61B 5/022 600/500 |
| 2004/0249297 | A1* | 12/2004 | Pfeiffer | A61B 5/1135 600/526 |
| 2005/0018890 | A1* | 1/2005 | McDonald | G06T 7/12 382/199 |
| 2005/0043609 | A1* | 2/2005 | Murphy | G16H 50/50 600/408 |
| 2005/0113665 | A1* | 5/2005 | Mohr | A61B 6/032 600/407 |
| 2005/0137661 | A1* | 6/2005 | Sra | A61B 8/5238 607/96 |
| 2006/0025689 | A1* | 2/2006 | Chalana | A61B 8/483 600/456 |
| 2006/0058618 | A1* | 3/2006 | Nishiura | A61B 8/463 600/407 |
| 2006/0082677 | A1* | 4/2006 | Donomae | G06T 5/008 348/362 |
| 2006/0122512 | A1* | 6/2006 | Abe | A61B 8/0883 600/454 |
| 2006/0241449 | A1* | 10/2006 | Oonuki | A61B 8/00 600/443 |
| 2006/0253031 | A1* | 11/2006 | Altmann | A61B 8/12 600/466 |
| 2007/0014452 | A1* | 1/2007 | Suresh | G06T 7/0012 382/128 |
| 2007/0083105 | A1* | 4/2007 | Miyazaki | G01R 33/5617 600/410 |
| 2007/0106146 | A1* | 5/2007 | Altmann | A61B 6/5247 600/407 |
| 2007/0167733 | A1* | 7/2007 | Miyoshi | G01R 33/5635 600/410 |
| 2007/0167777 | A1* | 7/2007 | Abe | G01S 15/8979 600/441 |
| 2007/0248319 | A1* | 10/2007 | Sakaguchi | A61B 6/504 386/232 |
| 2008/0085042 | A1* | 4/2008 | Trofimov | A61B 6/032 600/407 |
| 2008/0118126 | A1* | 5/2008 | Sakaguchi | A61B 6/463 382/128 |
| 2008/0170770 | A1* | 7/2008 | Suri | G06T 7/0012 382/128 |
| 2008/0181479 | A1* | 7/2008 | Yang | A61B 8/08 600/443 |
| 2008/0281218 | A1* | 11/2008 | Lei | A61B 6/503 600/523 |
| 2008/0285819 | A1* | 11/2008 | Konofagou | A61B 8/485 382/128 |
| 2008/0312527 | A1* | 12/2008 | Masumoto | G06T 7/0012 600/425 |
| 2009/0052613 | A1* | 2/2009 | Sakaguchi | G01N 23/046 378/8 |
| 2009/0054776 | A1* | 2/2009 | Sasaki | A61B 8/483 600/443 |
| 2009/0082675 | A1* | 3/2009 | Gunji | A61B 8/14 600/459 |
| 2009/0136109 | A1* | 5/2009 | Saigo | A61B 8/0858 600/443 |
| 2009/0148020 | A1* | 6/2009 | Sugiura | G06T 19/00 345/530 |
| 2009/0149734 | A1* | 6/2009 | Sugiura | G01R 33/5676 378/4 |
| 2009/0163815 | A1* | 6/2009 | Kawagishi | A61B 5/316 600/453 |
| 2009/0207241 | A1* | 8/2009 | Igarashi | G06T 7/507 348/E7.086 |
| 2009/0234220 | A1 | 9/2009 | Maschke | |
| 2009/0287303 | A1* | 11/2009 | Carpentier | A61F 2/2448 623/2.36 |
| 2009/0292175 | A1* | 11/2009 | Akimoto | A61B 1/2676 382/128 |
| 2009/0311655 | A1* | 12/2009 | Karkanias | G09B 5/065 434/262 |
| 2009/0312648 | A1* | 12/2009 | Zhang | A61B 6/541 600/513 |
| 2010/0027861 | A1* | 2/2010 | Shekhar | G06V 10/755 382/128 |
| 2010/0081917 | A1* | 4/2010 | Zhang | G16H 50/30 600/407 |

(56) References Cited

U.S. PATENT DOCUMENTS

| | | | |
|---|---|---|---|
| 2010/0128943 A1* | 5/2010 | Matsue | G16H 30/20 382/128 |
| 2010/0174191 A1* | 7/2010 | Lin | A61B 8/145 600/509 |
| 2010/0195887 A1* | 8/2010 | Abe | G06T 7/246 600/443 |
| 2010/0208957 A1* | 8/2010 | Chen | G06T 7/0016 382/128 |
| 2010/0317976 A1* | 12/2010 | Chelma | A61B 5/021 600/485 |
| 2011/0160849 A1* | 6/2011 | Carpentier | A61F 2/2445 623/2.19 |
| 2011/0218427 A1* | 9/2011 | Kitamura | A61B 6/5211 600/425 |
| 2011/0282151 A1* | 11/2011 | Trovato | G06T 7/74 600/117 |
| 2012/0053408 A1* | 3/2012 | Miyamoto | G06T 7/74 600/109 |
| 2012/0087561 A1* | 4/2012 | Guetter | G06T 7/174 382/131 |
| 2012/0089016 A1* | 4/2012 | Mizuno | G06T 11/206 600/425 |
| 2012/0093278 A1* | 4/2012 | Tsukagoshi | G06T 11/008 345/682 |
| 2012/0101368 A1* | 4/2012 | Masumoto | A61B 6/503 600/420 |
| 2012/0232853 A1* | 9/2012 | Voigt | G16H 50/50 703/11 |
| 2012/0281901 A1* | 11/2012 | Yoshizawa | A61B 5/055 382/134 |
| 2012/0302870 A1* | 11/2012 | Bjallmark | A61B 8/0883 600/443 |
| 2013/0012835 A1* | 1/2013 | Chono | A61B 8/467 600/587 |
| 2013/0013278 A1* | 1/2013 | Hu | G06T 7/0016 703/11 |
| 2013/0034287 A1* | 2/2013 | Itagaki | G01R 33/5635 382/131 |
| 2013/0053664 A1* | 2/2013 | Jian | A61B 5/021 600/324 |
| 2013/0137926 A1* | 5/2013 | Itai | A61B 1/04 600/111 |
| 2013/0267835 A1* | 10/2013 | Edwards | A61B 34/20 600/424 |
| 2013/0285655 A1* | 10/2013 | Miyazaki | G01R 33/34 324/309 |
| 2013/0336450 A1* | 12/2013 | Kyriakou | A61B 6/486 378/62 |
| 2014/0081079 A1* | 3/2014 | Kawasaki | G06T 7/0012 600/103 |
| 2014/0111201 A1* | 4/2014 | Kim | G01R 33/4835 324/309 |
| 2014/0121496 A1* | 5/2014 | Bi | G01R 33/56325 600/413 |
| 2015/0020547 A1* | 1/2015 | Akita | D04B 15/66 66/232 |
| 2015/0038860 A1* | 2/2015 | Fonte | A61B 6/507 600/505 |
| 2015/0145953 A1* | 5/2015 | Fujie | A61B 90/37 348/45 |
| 2015/0178938 A1* | 6/2015 | Gorman, III | G06T 7/174 382/131 |
| 2015/0190038 A1* | 7/2015 | Sakuragi | A61B 1/00193 348/45 |
| 2015/0193966 A1* | 7/2015 | Sakuragi | A61B 6/5247 382/128 |
| 2015/0237325 A1* | 8/2015 | Angot | A61B 90/361 348/47 |
| 2015/0245772 A1* | 9/2015 | Kawamoto | A61B 5/0205 600/494 |
| 2015/0257655 A1* | 9/2015 | Ishii | G16H 50/30 600/508 |
| 2016/0038048 A1* | 2/2016 | Ting | A61B 5/02405 600/479 |
| 2016/0061920 A1* | 3/2016 | Mekkaoui | G06T 7/11 382/131 |
| 2016/0063707 A1* | 3/2016 | Masumoto | A61B 90/37 345/441 |
| 2016/0070877 A1* | 3/2016 | Taylor | A61B 5/0044 703/9 |
| 2016/0100766 A1* | 4/2016 | Yoshioka | A61B 5/0082 600/301 |
| 2016/0125596 A1* | 5/2016 | Jo | G01R 33/5608 382/131 |
| 2016/0220190 A1* | 8/2016 | Zhang | A61B 5/7253 |
| 2016/0269713 A1* | 9/2016 | Kasumi | G02B 23/2484 |
| 2016/0310077 A1* | 10/2016 | Hunter | A61B 5/6862 |
| 2017/0065230 A1* | 3/2017 | Sinha | A61B 5/7221 |
| 2017/0084036 A1* | 3/2017 | Pheiffer | G06T 7/35 |
| 2017/0188986 A1* | 7/2017 | Nakagawa | A61B 6/52 |
| 2017/0245835 A1* | 8/2017 | Okazaki | A61B 8/0841 |
| 2017/0252000 A1* | 9/2017 | Fukuda | A61B 8/0883 |
| 2017/0296055 A1* | 10/2017 | Gardner | G01N 21/314 |
| 2017/0311839 A1* | 11/2017 | Osman | A61B 5/02028 |
| 2017/0347975 A1* | 12/2017 | Ishii | A61B 6/463 |
| 2017/0367659 A1* | 12/2017 | Lading | A61B 8/04 |
| 2018/0020932 A1* | 1/2018 | Chen | A61B 5/0261 600/479 |
| 2018/0055364 A1* | 3/2018 | Pierro | A61B 5/0059 |
| 2018/0108138 A1* | 4/2018 | Kluckner | G06T 7/11 |
| 2018/0150929 A1* | 5/2018 | Pheiffer | A61B 34/10 |
| 2018/0153621 A1* | 6/2018 | Duindam | G06T 7/337 |
| 2018/0184920 A1* | 7/2018 | Rabinovich | A61B 5/681 |
| 2018/0246178 A1* | 8/2018 | Wang | G01V 3/14 |
| 2018/0263503 A1* | 9/2018 | Ukawa | A61B 5/02108 |
| 2018/0289270 A1* | 10/2018 | Zalevsky | A61B 5/02444 |
| 2019/0089895 A1* | 3/2019 | Kono | A61B 1/000094 |
| 2019/0090818 A1* | 3/2019 | Nakajima | A61B 5/0205 |
| 2019/0167233 A1* | 6/2019 | Konofagou | A61B 8/486 |
| 2019/0239861 A1* | 8/2019 | Kobayashi | A61B 8/463 |
| 2019/0247127 A1* | 8/2019 | Kopel | A61B 6/12 |
| 2019/0247142 A1* | 8/2019 | Themelis | A61B 5/0071 |
| 2019/0290247 A1* | 9/2019 | Popovic | A61B 1/0005 |
| 2019/0298290 A1* | 10/2019 | Noji | A61B 6/488 |
| 2019/0304107 A1* | 10/2019 | Sakuragi | G09G 5/36 |
| 2019/0304129 A1* | 10/2019 | Schafer | A61B 1/00009 |
| 2019/0347814 A1* | 11/2019 | Ganapati | A61B 1/00194 |
| 2019/0357854 A1* | 11/2019 | Reich | A61B 5/02233 |
| 2019/0380781 A1* | 12/2019 | Tsai | A61B 5/067 |
| 2020/0060528 A1* | 2/2020 | Akimoto | G02B 23/24 |
| 2020/0077869 A1* | 3/2020 | Ida | G02B 23/2415 |
| 2020/0085281 A1* | 3/2020 | Regensburger | A61B 6/4441 |
| 2020/0085315 A1* | 3/2020 | Kang | A61B 5/6843 |
| 2020/0085579 A1* | 3/2020 | Kim | A61B 34/10 |
| 2020/0146568 A1* | 5/2020 | Park | A61B 5/7267 |
| 2020/0183013 A1* | 6/2020 | Iguchi | G01S 7/486 |
| 2020/0184723 A1* | 6/2020 | Ouyang | G06F 18/22 |
| 2020/0187897 A1* | 6/2020 | Abe | A61B 8/5223 |
| 2020/0219272 A1* | 7/2020 | Pizer | G06V 20/40 |
| 2020/0273148 A1* | 8/2020 | Ouyang | G06T 7/564 |
| 2020/0345215 A1* | 11/2020 | Springer | A61B 1/000095 |
| 2020/0345291 A1* | 11/2020 | Bradley | A61B 1/000094 |
| 2020/0383588 A1* | 12/2020 | Fujita | A61B 5/02108 |
| 2020/0387706 A1* | 12/2020 | Zur | G06T 15/08 |
| 2021/0015340 A1* | 1/2021 | Horie | A61B 1/009 |
| 2021/0052146 A1* | 2/2021 | Komp | A61B 1/00172 |
| 2021/0052240 A1* | 2/2021 | Weingarten | G06T 7/33 |
| 2021/0068683 A1* | 3/2021 | Reich | A61M 5/142 |
| 2021/0089079 A1* | 3/2021 | Kang | G06F 1/1684 |
| 2021/0121079 A1* | 4/2021 | Sugo | A61B 5/318 |
| 2021/0146117 A1* | 5/2021 | Reich | A61B 5/7275 |
| 2021/0153745 A1* | 5/2021 | Park | G16H 40/63 |
| 2021/0153752 A1* | 5/2021 | Park | A61B 5/1176 |
| 2021/0153756 A1* | 5/2021 | Hu | A61B 5/721 |
| 2021/0158526 A1* | 5/2021 | Patil | A61B 5/055 |
| 2021/0196386 A1* | 7/2021 | Shelton, IV | A61B 90/361 |
| 2021/0216822 A1* | 7/2021 | Paik | G16H 15/00 |
| 2021/0280312 A1* | 9/2021 | Freedman | G06V 10/764 |
| 2021/0386299 A1* | 12/2021 | Hocking | A61B 5/02255 |
| 2021/0398304 A1* | 12/2021 | Uyama | A61B 1/0638 |
| 2022/0020118 A1* | 1/2022 | Hallen | A61B 5/7203 |

(56) References Cited

U.S. PATENT DOCUMENTS

| | | | |
|---|---|---|---|
| 2022/0020166 A1* | 1/2022 | Hufford | G06V 10/25 |
| 2022/0039666 A1* | 2/2022 | Park | A61B 5/0205 |
| 2022/0104790 A1* | 4/2022 | Cadieu | A61B 8/463 |
| 2022/0222825 A1* | 7/2022 | Yaacobi | G06T 3/4007 |
| 2022/0248962 A1* | 8/2022 | Chu | A61B 5/02108 |
| 2022/0265149 A1* | 8/2022 | Lee | A61B 5/14546 |
| 2022/0296111 A1* | 9/2022 | Leabman | A61B 5/681 |
| 2022/0313214 A1* | 10/2022 | Ando | A61B 8/5246 |
| 2022/0409071 A1* | 12/2022 | Leaning | A61B 5/7235 |

FOREIGN PATENT DOCUMENTS

| | | |
|---|---|---|
| JP | 2016-062488 A | 4/2016 |
| JP | 2016-179121 A | 10/2016 |
| JP | 6095879 B1 | 3/2017 |
| JP | 2017-153953 A | 9/2017 |
| WO | WO 2017/073181 A1 | 5/2017 |

* cited by examiner

FIG.9

RECORDING DEVICE, IMAGE OBSERVATION DEVICE, OBSERVATION SYSTEM, CONTROL METHOD OF OBSERVATION SYSTEM, AND COMPUTER-READABLE RECORDING MEDIUM

CROSS-REFERENCE TO RELATED APPLICATION

This application is a continuation of International Application No. PCT/JP2018/032248, filed on Aug. 30, 2018, the entire contents of which are incorporated herein by reference.

BACKGROUND

1. Technical Field

The present disclosure relates to a recording device, an image observation device, an observation system, a control method of the observation system, and a computer-readable recording medium.

2. Related Art

Observation of the inside of the bodies of subjects, which are living bodies, using endoscopes has been performed in the medical field (for example, see Japanese Patent Application Laid-open No. 2016-062488). Images captured by an endoscope are used in diagnosis performed by a first medical doctor operating the endoscope.

Studies have been made on: storage of the images captured by the endoscope into a recording device; and use of the stored images for diagnosis (a second opinion) by a second medical doctor who is at a place spatially or temporally away from where the first medical doctor is.

However, biological information of the subject such as pulse and respiration is not available when the second medical doctor observes the stored images, which makes diagnosis more difficult than when the subject is directly observed by inserting the endoscope into the body.

SUMMARY

The disclosure addresses the above-described issue, and a general purpose thereof is to provide a recording device, an image observation device, an observation system, a control method of the observation system, and an operating program for the observation system that facilitate the observation using the recorded images captured by an endoscope.

To address the above issue, in some embodiments, a recording device includes: a memory; and a processor including hardware. The processor is configured to generate, based on temporal change in plural sets of image data that have been generated by an endoscope and arranged chronologically, biological information on a subject, associate the plural sets of image data with the biological information to record the plural sets of image data with the biological information into the memory, and select, based on the biological information, image data from the plural sets of image data that have been recorded in the memory to generate three-dimensional image data.

In some embodiments, an image observation device includes: a processor comprising hardware. The processor is configured to acquire data on a three-dimensional image, the data being generated by selection of a set of image data from plural sets of image data that have been generated by an endoscope and arranged chronologically, the selection being based on biological information on a subject, the biological information being generated based on temporal change in the plural sets of image data, generate angle-of-view information, based on information of a position and an angle at which the subject is observed, and generate two-dimensional image data acquired by observation of the three-dimensional image, the observation being based on the biological information and the angle-of-view information.

In some embodiments, an observation system includes: a memory; and a processor including hardware. The processor is configured to generate, based on temporal change in plural sets of image data that have been generated by an endoscope and arranged chronologically, biological information on a subject, associate the plural sets of image data with the biological information to record the plural sets of image data with the biological information into the memory, select, based on the biological information, image data from the plural sets of image data that have been recorded in the memory to generate data on a three-dimensional image, generate angle-of-view information, based on information of a position and an angle at which the subject is observed, and generate two-dimensional image data acquired by observation of the three-dimensional image, the observation being based on the biological information and the angle-of-view information.

In some embodiments, a control method of an observation system includes: generating, based on temporal change in plural sets of image data that have been generated by an endoscope and arranged chronologically, biological information on a subject; selecting, based on the biological information, image data from the plural sets of image data to generate data on a three-dimensional image; generating angle-of-view information, based on information of a position and an angle at which the subject is observed; and generating two-dimensional image data acquired by observation of the three-dimensional image, the observation being based on the biological information and the angle-of-view information.

In some embodiments, provided is a non-transitory computer-readable recording medium with an executable program stored thereon. The program causes an observation system to execute: generating, based on temporal change in plural sets of image data that have been generated by an endoscope and arranged chronologically, biological information on a subject; selecting, based on the biological information, image data from the plural sets of image data to generate data on a three-dimensional image; generating angle-of-view information, based on information of a position and an angle at which the subject is observed; and generating two-dimensional image data acquired by observation of the three-dimensional image, the observation being based on the biological information and the angle-of-view information.

The above and other features, advantages and technical and industrial significance of this disclosure will be better understood by reading the following detailed description of presently preferred embodiments of the disclosure, when considered in connection with the accompanying drawings.

DETAILED DESCRIPTION

Embodiments of a recording device, an image observation device, an observation system, a control method of the observation system, and an operating program for the observation system will be described below by reference to the drawings. The disclosure is not limited by these embodiments. The disclosure is generally applicable to recording devices using medical endoscopes, image observation devices using medical endoscopes, observation systems using medical endoscopes, control methods for the observation systems, and operating programs for the observation systems.

Any elements that are the same or corresponding to each other are assigned with the same reference sign throughout the drawings, as appropriate. In addition, it needs to be noted that the drawings are schematic and relations between dimensions of each element therein and proportions between the elements therein may be different from the actual ones. The drawings may also include a portion that differs in its dimensional relations or proportions between the drawings.

EMBODIMENTS

Figure 1:
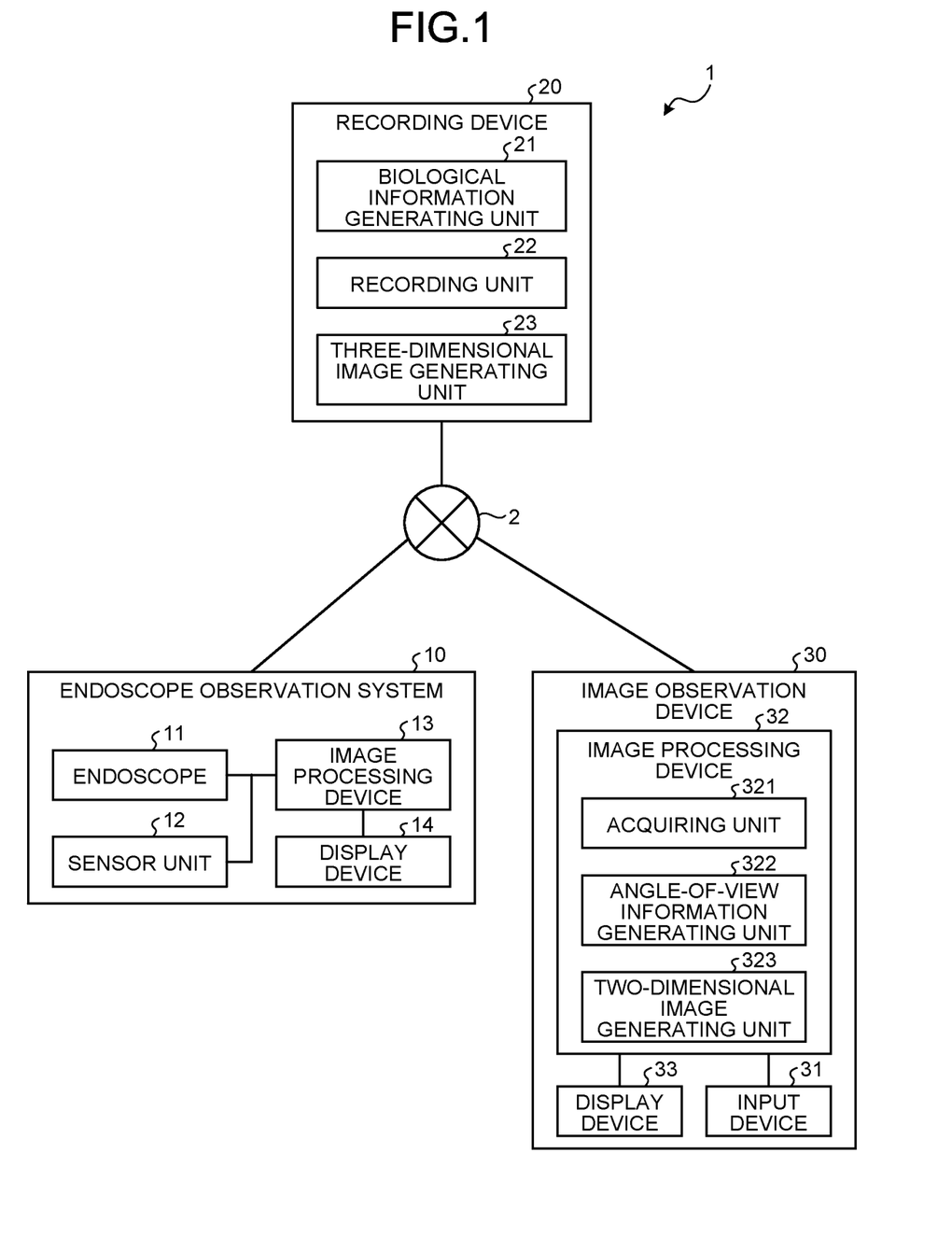
FIG. 1 is a block diagram illustrating a configuration of an observation system according to an embodiment of the disclosure.

FIG. 1 is a block diagram illustrating a configuration of an observation system according to an embodiment of the disclosure. As illustrated in FIG. 1, an observation system 1 according to this embodiment includes an endoscope observation system 10, a recording device 20, and an image observation device 30, which are connected to one another via a network 2, such as an Internet connection.

The endoscope observation system 10 includes: an endoscope 11 that captures an image of the inside of the body of a subject that is a living body; a sensor unit 12 that detects biological information on the subject; an image processing device 13 that performs image processing on image data captured by the endoscope 11; and a display device 14 that displays an image according to image data generated by the image processing device 13.

The endoscope 11 has an insertion unit to be inserted into the subject, and an operating unit that is connected consecutively to a proximal end of the insertion unit. According to input to the operating unit, an imaging device arranged at a distal end of the insertion unit captures an image of the inside of the body of the subject. The imaging device is an image sensor, such as a complementary metal oxide semiconductor (CMOS) or a charge coupled device (CCD).

The sensor unit 12 acquires biological information that is information on, for example, the pulse or respiration. Specifically, the sensor unit 12 is a bloodstream sensor that is fixed to hold a fingertip of the subject. Furthermore, the sensor unit 12 may be a respiration sensor attached to, for example, the mouth, nose, or chest of the subject.

The image processing device 13 is configured using a work station or personal computer including a general-purpose processor or a dedicated processor. The general purpose processor may be, for example, a central processing unit (CPU), and the dedicated processor may be any of various arithmetic circuits that execute specific functions, such as application specific integrated circuits (ASICs) and field programmable gate arrays (FPGAs).

The display device 14 is configured using liquid crystal or organic electroluminescence, for example.

The recording device 20 is a server connected to plural devices, such as an endoscope observation system and an image observation device, including the endoscope observation system 10 and the image observation device 30, via the network 2. The recording device 20 is implemented by, for example: a general-purpose processor, such as a CPU, or a dedicated processor, such as an arithmetic circuit that executes a specific function; a recording medium (a memory device), such as a semiconductor memory, an HDD, an MO, a CD-R, or a DVD-R; and a drive device that drives the recording medium. The arithmetic circuit may be an ASIC or FPGA, and the semiconductor memory may be a flash memory, a random access memory (RAM), or a read only memory (ROM).

The recording device 20 includes: a biological information generating unit 21 that generates biological information on the subject; a recording unit 22 that records therein plural sets of image data in association with the biological information, the plural sets of image data having been generated by the endoscope 11 and chronologically arranged; and a three-dimensional image generating unit 23 that generates three-dimensional image data by selecting, based on the biological information, image data from the plural sets of image data that have been recorded in the recording unit 22.

The image observation device 30 includes: an input device 31 that receives input of a position and an angle, at which the subject is observed; an image processing device 32 that reads three-dimensional image data recorded in the recording device 20 and generates image data; and a display device 33 that displays an image according to the image data generated by the image processing device 32.

The input device 31 has a configuration similar to that of the operating unit of the endoscope 11 and receives input of a position and an angle, at which the subject is observed. However, the input device 31 may be formed of, for example, at least one selected from the group of a mouse, a keyboard, a touch pad, and a touch panel.

The image processing device 32 is configured using a work station or personal computer including, for example, a general-purpose processor, such as a CPU, or a dedicated processor, such as an arithmetic circuit that executes a specific function. The arithmetic circuit may be an ASIC or FPGA.

The image processing device 32 has: an acquiring unit 321 that acquires the three-dimensional image data generated by the three-dimensional image generating unit 23; an angle-of-view information generating unit 322 that generates angle-of-view information, based on information received by the input device 31; and a two-dimensional image generating unit 323 that generates two-dimensional image data acquired by observation of a three-dimensional image, the observation being based on the biological information and the angle-of-view information.

The display device 33 is configured using liquid crystal or organic electroluminescence, for example.

Figure 2:
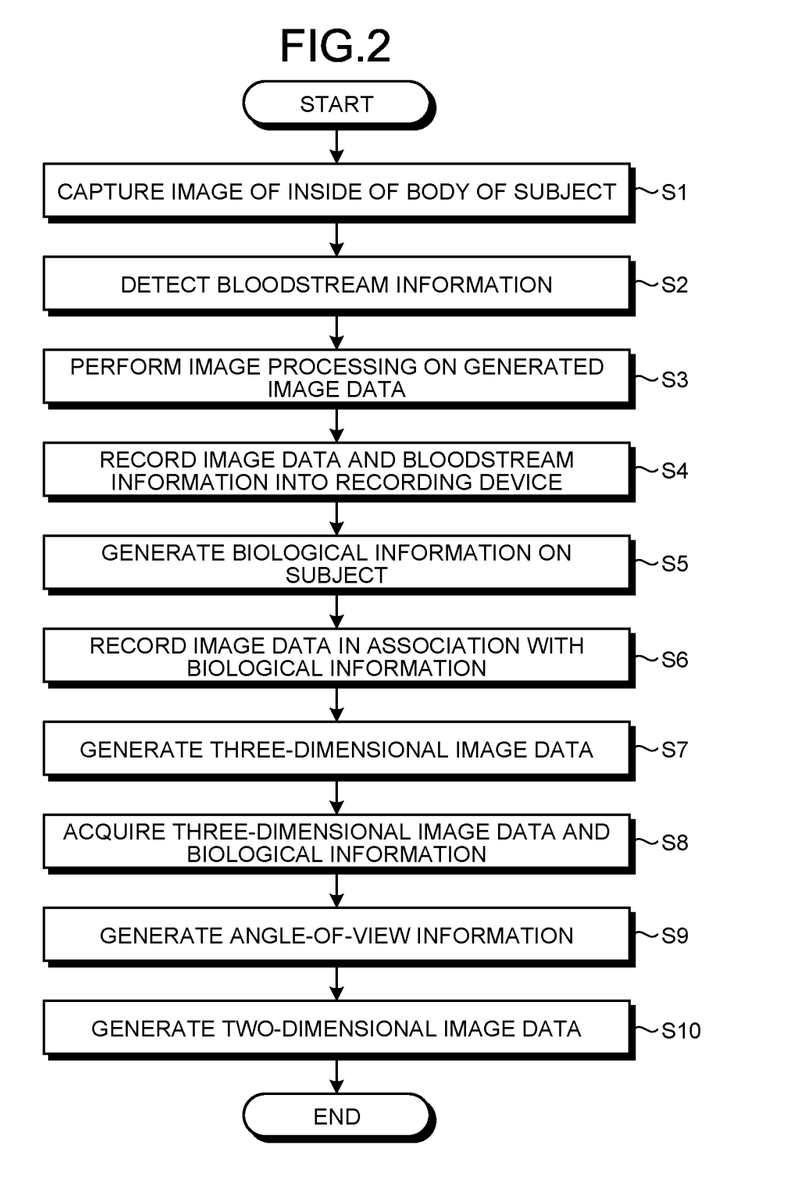
FIG. 2 is a flow chart for observation using the observation system.

Next, operation in which a second medical doctor observes an image using the image observation device 30 will be described, the image having been captured by a first medical doctor using the endoscope observation system 10. FIG. 2 is a flow chart for observation using an observation system. As illustrated in FIG. 2, by using the endoscope 11, the first medical doctor captures images of the inside of the body of a subject (Step S1).

Simultaneously, the sensor unit 12 detects bloodstream information for a time period in which the endoscope 11 is capturing the images (Step S2).

Subsequently, the image processing device 13 performs predetermined image processing on plural sets of image data generated by the endoscope 11 (Step S3).

Thereafter, the endoscope observation system 10 transmits the plural sets of image data and the bloodstream information via the network 2 to the recording device 20, and records the plural sets of image data and the bloodstream information into the recording device 20 (Step S4).

Figure 3:
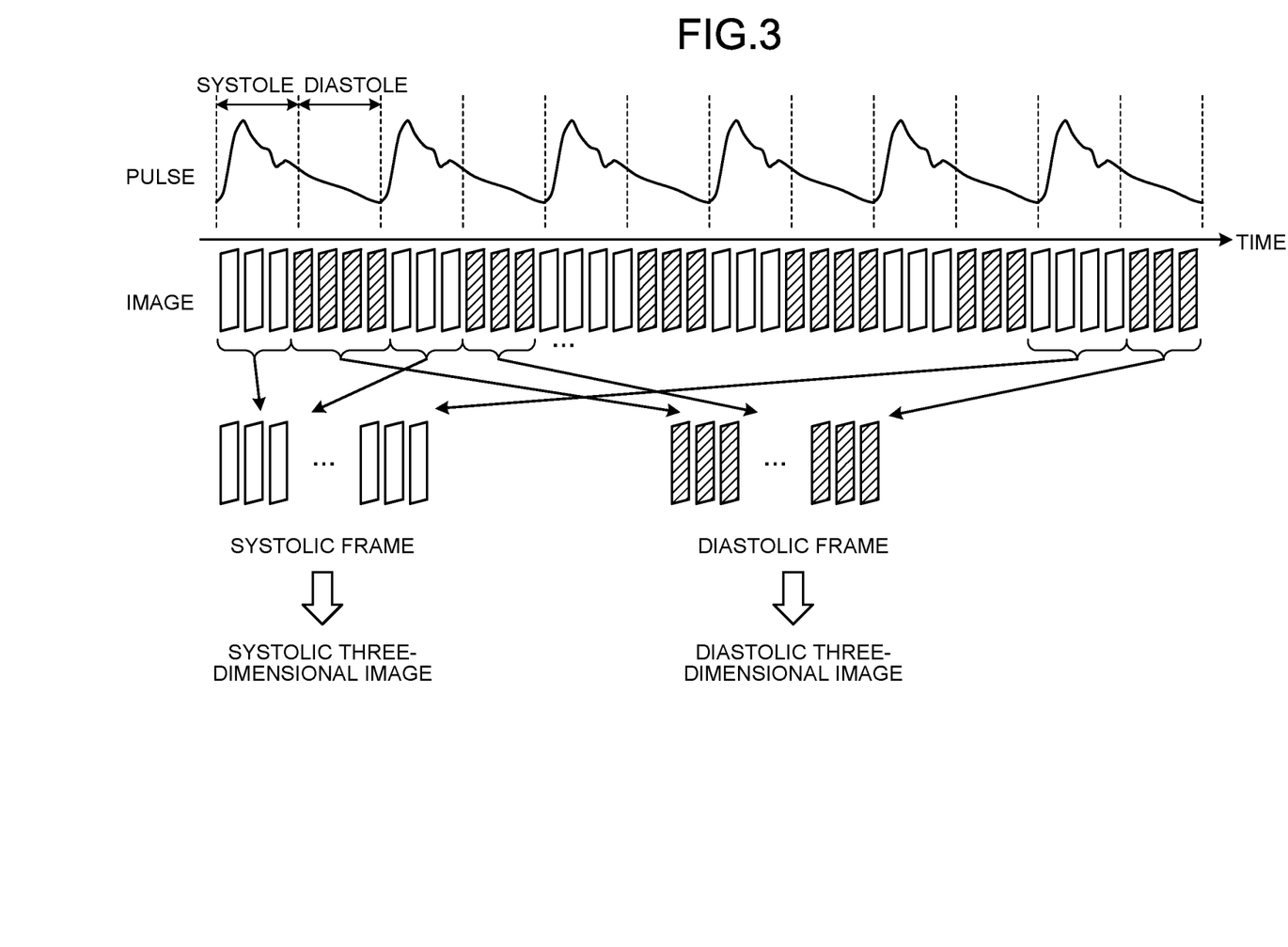
FIG. 3 is a diagram illustrating how a recording device generates three-dimensional image data.

Subsequently, the biological information generating unit 21 generates biological information that is pulse information, using the bloodstream information (Step S5: biological information generating step). FIG. 3 is a diagram illustrating how a recording device generates three-dimensional image data. As illustrated in FIG. 3, based on the bloodstream information detected by the sensor unit 12, the biological information generating unit 21 determines whether each image captured by the endoscope 11 is an image captured in the systole or an image captured in the diastole. A result of this determination is the pulse information on each image. Systole is a phase in which a heart contracts and blood is being sent out from the heart. On the contrary, diastole is a phase in which the heart dilates and the arterial blood pressure is low according to the systemic vascular resistance. The blood flow volumes in organs inside a body differ between the systole and the diastole, and color tones of the organs thus also differ between the systole and the diastole.

The recording unit 22 then records therein the plural sets of image data and the biological information in association with each other (Step S6). Specifically, the recording unit 22 records therein each image included in the plural sets of image data in association with pulse information on that image.

Furthermore, the three-dimensional image generating unit 23 generates three-dimensional image data by selecting image data, based on the biological information, from the plural sets of image data (Step S7: three-dimensional image generating step). Specifically, as illustrated in FIG. 3, the three-dimensional image generating unit 23 selects, from the plural sets of image data, an image of a systolic frame captured in the systole, and generates a systolic three-dimensional image. The three-dimensional image generating unit 23 selects, from the plural sets of image data, an image of a diastolic frame captured in the diastole, and generates a diastolic three-dimensional image. The three-dimensional image generating unit 23 generates a three-dimensional image by extracting feature points from each image and joining the feature points in consecutive images in the chronological order. The systolic three-dimensional image and the diastolic three-dimensional image generated by the three-dimensional image generating unit 23 are recorded into the recording unit 22.

Subsequently, the acquiring unit 321 of the image observation device 30 acquires the three-dimensional image data and the biological information (Step S8). Specifically, the acquiring unit 321 acquires the systolic three-dimensional image and the diastolic three-dimensional image from the recording unit 22 of the recording device 20.

Based on information received by the input device 31, the angle-of-view information generating unit 322 generates angle-of-view information (Step S9: angle-of-view information generating step). Specifically, based on operation on the input device 31 by the second medical doctor, the angle-of-view information generating unit 322 generates angle-of-view information that temporally changes.

Figure 4:
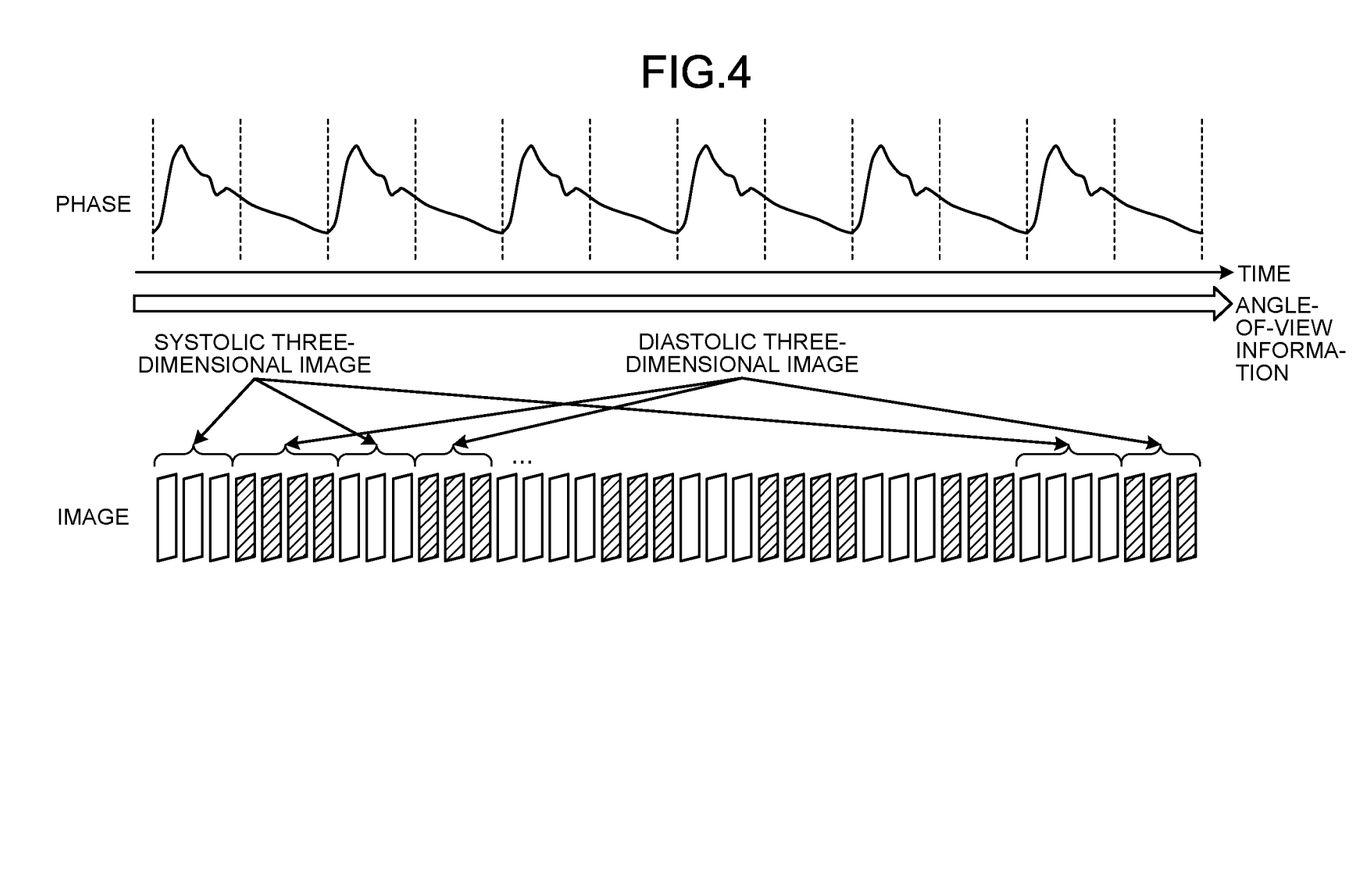
FIG. 4 is a diagram illustrating how an image observation device generates two-dimensional image data.

Furthermore, the two-dimensional image generating unit 323 generates two-dimensional image data acquired by observation of a three-dimensional image, the observation being based on biological information and angle-of-view information (Step S10: two-dimensional image generating step). FIG. 4 is a diagram illustrating how an image observation device generates two-dimensional image data. As illustrated in FIG. 4, based on pulse information, the two-dimensional image generating unit 323 generates a virtual pulse phase. This phase may be acquired by using the pulse information, or by calculating, based on the pulse information, the average value of periods or amplitudes, for example. Based on the phase and angle-of-view information, the two-dimensional image generating unit 323 generates, from a three-dimensional image corresponding to the phase, two-dimensional image data for a position and an angle indicated by the second medical doctor, the three-dimensional image being the systolic three-dimensional image or the diastolic three-dimensional image.

As described above, the embodiment enables the second medical doctor to observe the inside of the body of a subject that is virtually pulsating and has changing bloodstream. That is, observation is facilitated because the second medical doctor is able to perform observation as if the second medical doctor is directly observing the inside of the body of the subject using the endoscope 11.

Furthermore, when respiration information is used as the biological information, the second medical doctor is able to observe the inside of the body of a subject that virtually moves due to aspiration. That is, observation is facilitated because the second medical doctor is able to perform observation as if the second medical doctor is directly observing the inside of the body of the subject using the endoscope 11.

According to the above description of the embodiment, a virtual pulse is generated for observation of the inside of the body of a subject, but the systolic three-dimensional image or the diastolic three-dimensional image may be observed as is.

First Modified Example

Figure 5:
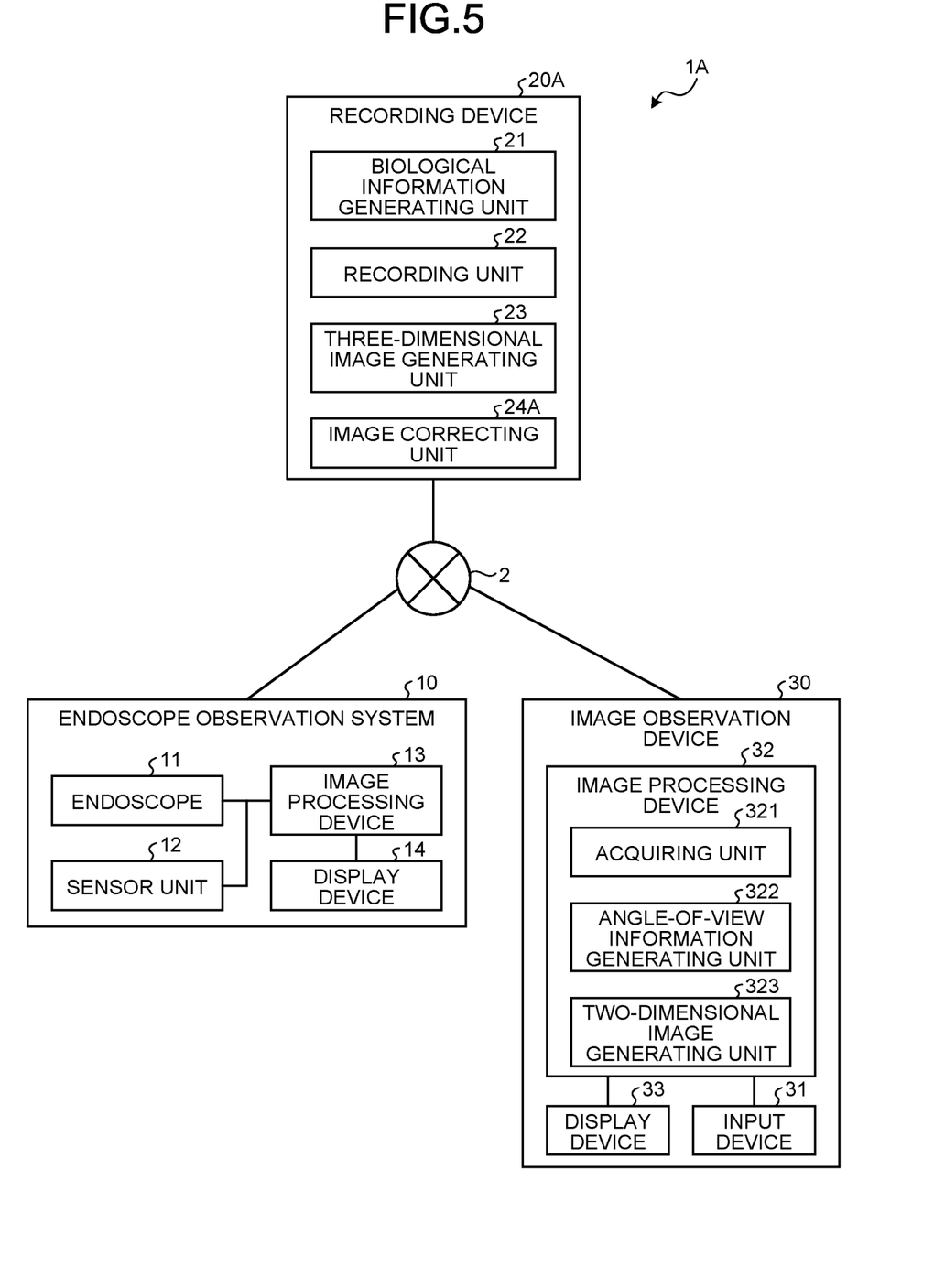
FIG. 5 is a block diagram illustrating a configuration of an observation system according to a first modified example.

FIG. 5 is a block diagram illustrating a configuration of an observation system according to a first modified example. As illustrated in FIG. 5, a recording device 20A in an observation system 1A further includes an image correcting unit 24A that performs correction including: reducing change in shape that differs according to biological information; and enhancing change in color tones that differ according to the biological information. Specifically, the image correcting unit 24A corrects shape information and color tone information on the systolic three-dimensional image and the diastolic three-dimensional image illustrated in FIG. 3. Shape information is, for example, three-dimensional coordinate values of feature points extracted when a three-dimensional image is generated, and color tone information is, for example, RGB signal values of the feature points.

When the shape information on the systolic three-dimensional image is Ss, the shape information on the diastolic three-dimensional image is Se, the corrected shape information on the systolic three-dimensional image is Ss', the corrected shape information on the diastolic three-dimensional image is Se', and the correction coefficient is ks; the correction for reducing the change in shape is able to be performed on a three-dimensional image by using the following Equations (1) and (2).

$$Ss'=Ss+ks(Se-Ss), \text{ where } 0<ks<0.5 \quad (1)$$

$$Se'=Se-ks(Se-Ss) \text{ where } 0<ks<0.5 \quad (2)$$

Furthermore, when the color tone information on the systolic three-dimensional image is Ts, the color tone information on the diastolic three-dimensional image is Te, the corrected color tone information on the systolic three-dimensional image is Ts', the corrected color tone information on the diastolic three-dimensional image is Te', and the correction coefficient is kt; the correction for enhancing the change in color tones in a three-dimensional image is able to be performed by using the following Equations (3) and (4).

$$Ts'=Ts+ks(Te-Ts) \text{ where } kt<0 \quad (3)$$

$$Te'=Te-ks(Te-Ts) \text{ where } kt<0 \quad (4)$$

As described above, by the image correcting unit 24A performing the correction, the change in shape between the systolic three-dimensional image and the diastolic three-dimensional image generated by the three-dimensional image generating unit 23 is reduced, and unnecessary movement due to the pulse, for example, in the two-dimensional image data is thus eliminated when the second medical doctor performs observation and the observation is thus facilitated. Furthermore, by the image correcting unit 24A implementing the correction, the change in color tones between the systolic three-dimensional image and the diastolic three-dimensional image is increased, and the second medical doctor is able to easily observe a portion having a different color tone in the two-dimensional image data, the portion being, for example reddening or a tumor.

According to the above description of the first modified example, the image correcting unit 24A corrects each of the shapes and the color tones of the systolic three-dimensional image and the diastolic three-dimensional image, but the first modified example is not limited to this example. The three-dimensional image generating unit 23 may generate a shape of a three-dimensional image using all of images, generate a systolic three-dimensional image using systolic color tone information for the generated shape of the three-dimensional image, and generate a diastolic three-dimensional image using diastolic color tone information for the generated shape of the three-dimensional image. The image correcting unit 24A may then correct only the color tones of the systolic three-dimensional image and the diastolic three-dimensional image by using Equations (3) and (4) above. Similarly, the image correcting unit 24A may correct only the shapes of three-dimensional images generated by the three-dimensional image generating unit 23.

According to the above description of the first modified example, the image correcting unit 24A corrects the systolic three-dimensional image and the diastolic three-dimensional image, but the first modified example is not limited to this example. The image correcting unit 24A may, for example, correct the image data generated by the endoscope 11, and the three-dimensional image generating unit 23 may generate three-dimensional image data using the corrected image data.

Second Modified Example

Figure 6:
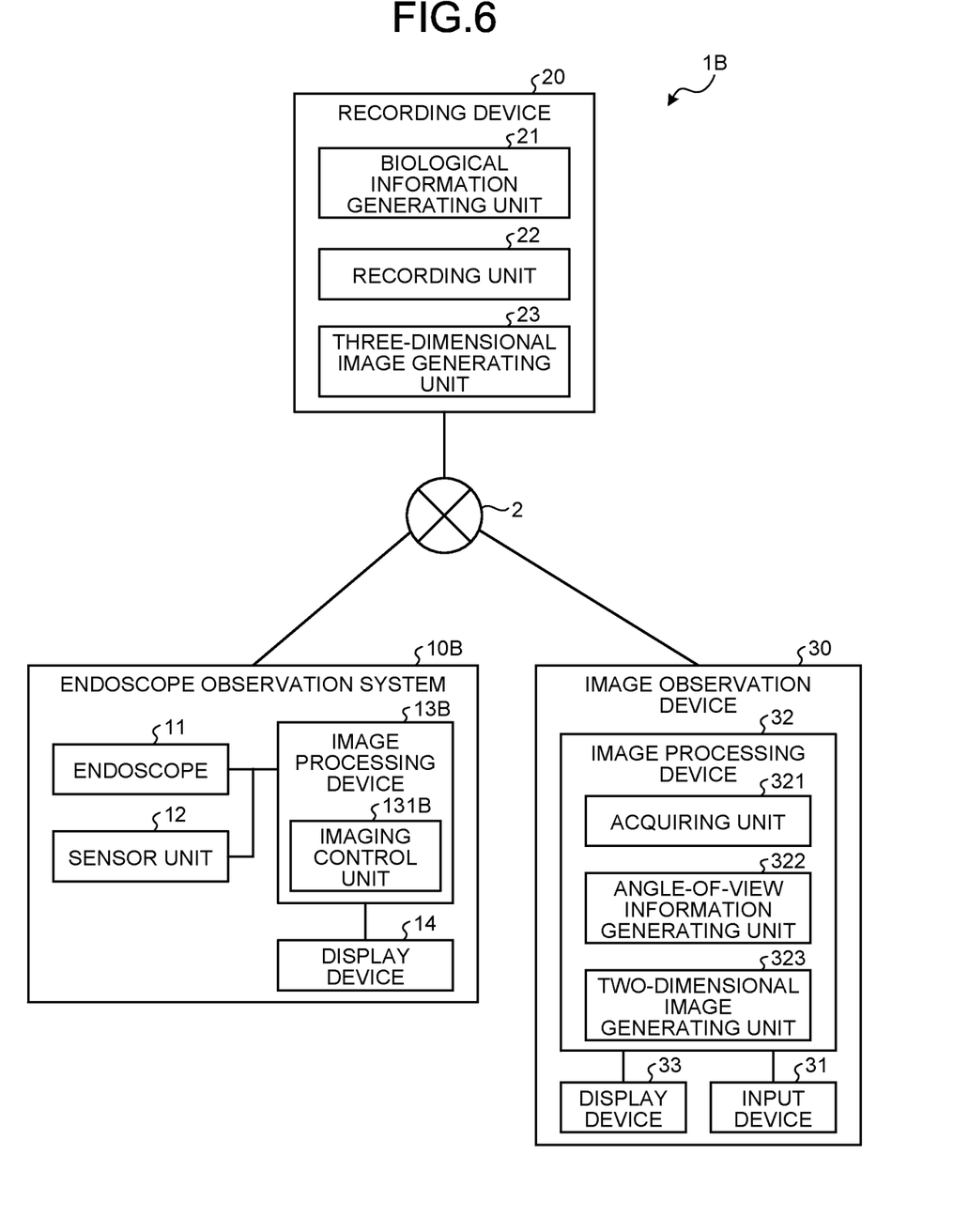
FIG. 6 is a block diagram illustrating a configuration of an observation system according to a second modified example.

FIG. 6 is a block diagram illustrating a configuration of an observation system according to a second modified example. As illustrated in FIG. 6, an image processing device 13B of an endoscope observation system 10B in an observation system 1B further includes an imaging control unit 131B that controls the timing for imaging by the endoscope 11, according to biological information. As a result, imaging is enabled at times when the bloodstream becomes the maximum and the minimum, for example. The second medical doctor is then able to perform observation in a state where the differences between the systole and the diastole are large and thus the observation is facilitated.

Third Modified Example

Figure 7:
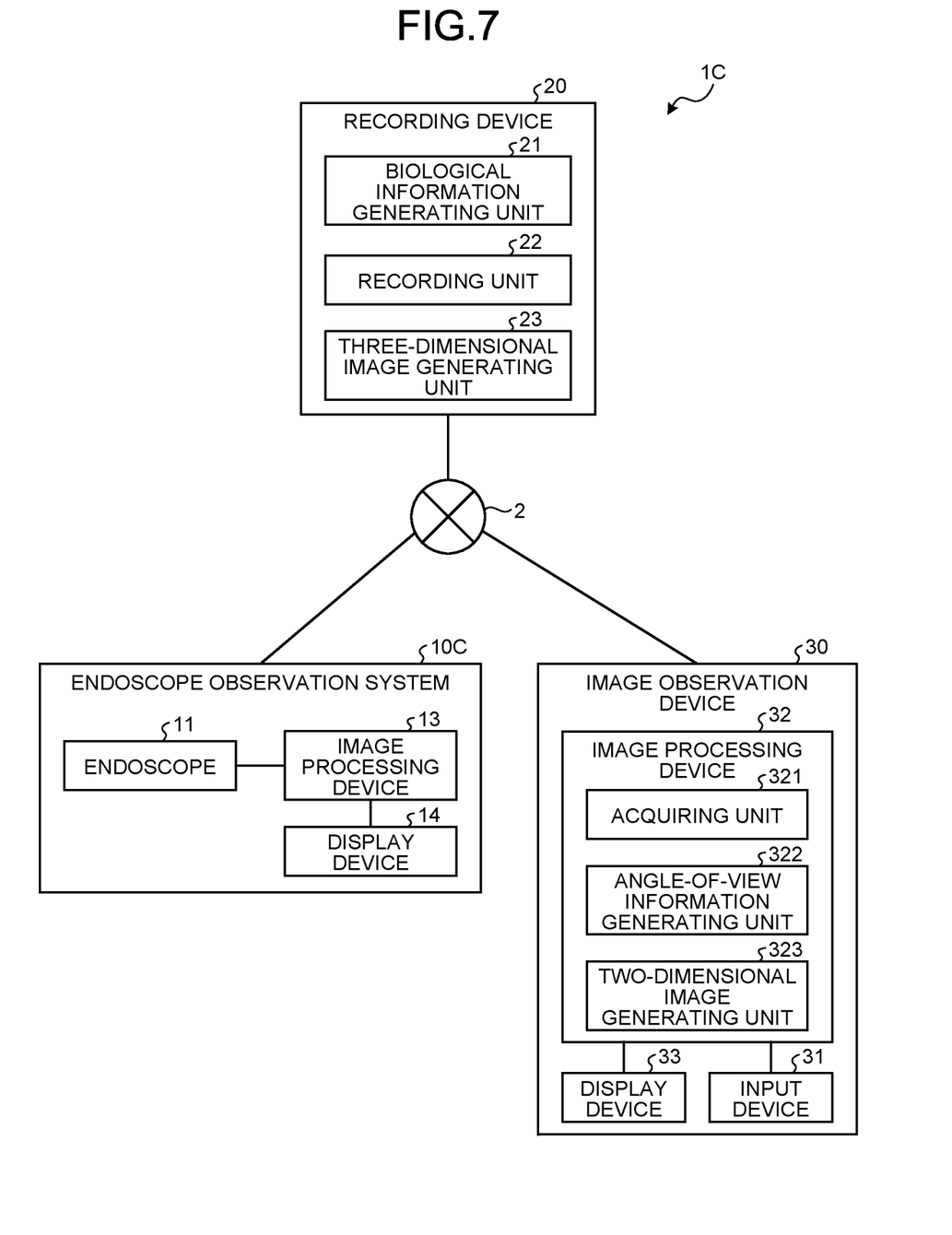
FIG. 7 is a block diagram illustrating a configuration of an observation system according to a third modified example.

FIG. 7 is a block diagram illustrating a configuration of an observation system according to a third modified example. As illustrated in FIG. 7, an endoscope observation system 100 in an observation system 10 does not have a sensor unit.

Based on temporal change in image data that have been recorded in the recording unit 22, the biological information generating unit 21 generates biological information.

Figure 8:
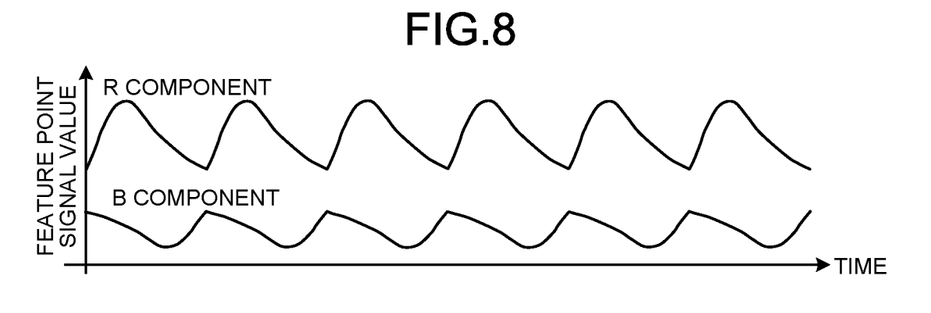
FIG. 8 is a diagram illustrating how biological information is generated from signal values of feature points.

FIG. 8 is a diagram illustrating how biological information is generated from signal values of feature points. As illustrated in FIG. 8, color tones of the inside of the body of a subject temporally change depending on the bloodstream. The biological information generating unit 21 generates biological information, based on temporal change in RGB signal values of feature points extracted upon generation of a three-dimensional image. Specifically, the biological information generating unit 21 generates, based on temporal change in signal values of the R component and B component of feature points, biological information that is pulse information like the one illustrated in FIG. 3. The biological information generating unit 21 may generate pulse information, based on, for example, temporal change in color tones of the whole image or temporal change in color tones of an area extracted by predetermined image processing. The biological information generating unit 21 may generate pulse information, based on information on any one of color components, such as the R component or the B component, or may generate pulse information by performing predetermined calculation with signal values of each color component.

Figure 9:
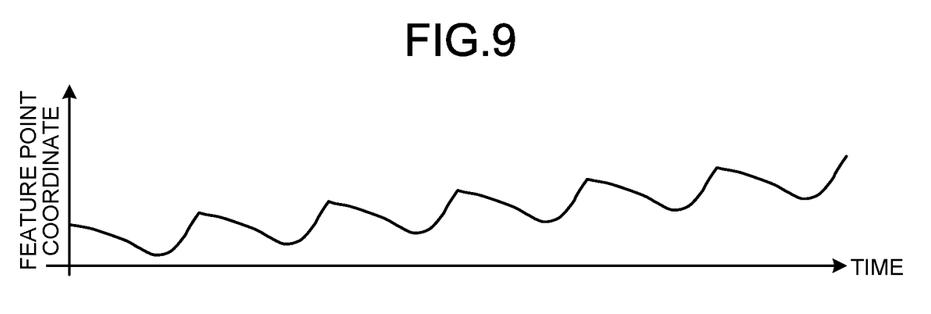
FIG. 9 is a diagram illustrating how biological information is generated from coordinate values of feature points.

FIG. 9 is a diagram illustrating how biological information is generated from coordinate values of feature points. As illustrated in FIG. 9, the position of an organ inside a subject temporally changes depending on the pulse. The biological information generating unit 21 generates biological information, based on temporal change in coordinate values of feature points extracted upon generation of a three-dimensional image. Specifically, the biological information generating unit 21 generates, based on temporal change in coordinates of feature points, biological information that is pulse information like the one illustrated in FIG. 3. The biological information generating unit 21 may generate pulse information, based on temporal change in coordinates of, for example, a contour detected from an image, without being limited to feature points.

According to the disclosure, a recording device, an image observation device, an observation system, a control method of the observation system, and an operating program for the observation system that further facilitate observation are able to be provided, the observation involving acquisition of images from the recording device, the images having been captured using an endoscope.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A recording device comprising:
a processor comprising hardware, the processor being configured to:
generate, based on temporal change in plural sets of image data that have been generated by an endoscope and arranged chronologically, pulse information on a subject;
associate the plural sets of image data with the pulse information to record the plural sets of image data with the pulse information into a memory; and
select, based on the pulse information, image data from the plural sets of image data that have been recorded in the memory to generate three-dimensional image data,
wherein the processor is further configured to perform correction to reduce change in shape that differs according to the pulse information and to enhance change in a color tone that differs according to the pulse information, and
wherein the processor is further configured to:
select image data in systole from the plural sets of image data that have been recorded in the memory to generate systolic three-dimensional image data, the systole being a phase in which a heart contracts and blood is being sent out from the heart;
select image data in diastole from the plural sets of image data that have been recorded in the memory to generate diastolic three-dimensional image data, the diastole being a phase in which the heart dilates and an arterial blood pressure is low according to a systemic vascular resistance; and
perform the correction to reduce change in shape between a systolic three-dimensional image and a diastolic three-dimensional image and to enhance change in color tone between the systolic three-dimensional image and the diastolic three-dimensional image.

2. The recording device according to claim 1, wherein the processor is further configured to:
extract feature points in images from the plural sets of image data that have been arranged chronologically; and
generate, based on temporal change in the extracted feature points, the pulse information on the subject.

3. The recording device according to claim 1, wherein the processor is further configured to:
extract feature points in images from the plural sets of image data that have been arranged chronologically; and
generate, based on temporal change in colors of the extracted feature points, the pulse information on the subject.

4. The recording device according to claim 1, wherein the processor is further configured to:
extract feature points in images from the plural sets of image data that have been arranged chronologically; and
generate, based on temporal change in coordinates of the extracted feature points, the pulse information on the subject.

* * * * *